| United States Patent [19] | [11] 4,011,137 |
|---|---|
| Thompson et al. | [45] Mar. 8, 1977 |

[54] PROCESS FOR PRODUCING DEXTROSE USING MIXED IMMOBILIZED ENZYMES

[75] Inventors: Kenneth N. Thompson; Richard A. Johnson; Norman E. Lloyd, all of Clinton, Iowa

[73] Assignee: Standard Brands Incorporated, New York, N.Y.

[22] Filed: Aug. 26, 1974

[21] Appl. No.: 500,975

[52] U.S. Cl. .............................. 195/31 R; 195/63; 195/68; 195/115; 195/DIG. 11
[51] Int. Cl.$^2$ ........................................ C12D 13/02
[58] Field of Search ..... 195/31 R, 63, 68, DIG. 11, 195/115, 13

[56] References Cited

UNITED STATES PATENTS

| 2,891,869 | 6/1959 | Langlois | 195/31 R |
|---|---|---|---|
| 3,627,638 | 12/1971 | Barker et al. | 195/68 |
| 3,715,277 | 2/1973 | Dinelli et al. | 195/63 |
| 3,720,583 | 3/1973 | Fisher | 195/31 R |
| 3,783,101 | 1/1974 | Tomb et al. | 195/68 |
| 3,809,613 | 5/1974 | Vieth et al. | 195/68 |
| 3,810,821 | 5/1974 | Barker et al. | 195/68 |
| 3,849,253 | 11/1974 | Harvey et al. | 195/68 |

FOREIGN PATENTS OR APPLICATIONS

| 2,404,101 | 8/1974 | Germany | 195/31 R |
|---|---|---|---|

OTHER PUBLICATIONS

Ustinnikov et al., "Hydrolysis of Starch During the Separation and Combined Action of α-Amylase and Glucoamylase Applicable to Conditions of Alcohol Production", Ferment Spirit Prom., 37(2), pp. 13–17 (1971).

Ustinnikov et al., "Hydrolysis of Starch During the Separate and Combined Action of α-Amylase and Glucoamylase Applicable to Alcohol Production", Chem. Abstracts, vol. 74, (1971) p. 410, 139529a.

Barker et al., "Enzyme Reactors for Industry", Process Biochem., vol. 6, No. 10, (Oct. 1971), pp. 11–13.

Weetall et al., "Continuous Production from Corn Starch, A study of Reactor Parameters Necessary for Commercial Application", Enzyme Engineering, Interscience Publishers, (1972), pp. 241–266.

Primary Examiner—A. Louis Monacell

[57] ABSTRACT

Process for converting starch to dextrose wherein a partially hydrolyzed starch solution containing at least 10 percent hydrolyzed starch is contacted with an enzyme system under conditions whereby substantially complete conversion of the starch to dextrose is achieved. The enzyme system comprises immobilized glucoamylase and alpha-amylase selected from the group consisting of soluble alpha-amylase, immobilized alpha-amylase and mixtures thereof.

17 Claims, No Drawings

PROCESS FOR PRODUCING DEXTROSE USING MIXED IMMOBILIZED ENZYMES

THE INVENTION

This invention relates to a process for converting starch to dextrose. More particularly, this invention relates to a process for converting starch to dextrose by the use of an enzyme system comprising immobilized glucoamylase and alpha-amylase selected from the group consisting of soluble alpha-amylase, immobilized alpha-amylase and mixtures thereof.

Processes for hydrolyzing starch to dextrose are well known in the art. These methods can be grouped into two broad categories. These are the acid-enzyme and the enzyme-enzyme conversion processes. In the acid-enzyme process, generally, starch is first partially hydrolyzed or liquefied, for instance, by forming an aqueous suspension containing from 35 to 40 percent starch and incorporating therein an acid such as hydrochloric acid. The suspension is then heated to relatively high temperatures to partially hydrolyze the starch and then cooled and treated with a glucoamylase preparation under suitable conditions to enzymatically convert the partially hydrolyzed starch to dextrose. The acid-enzyme process is disclosed, for example in U.S. Pat. Nos. 2,304,168, 2,531,999, 2,893,921 and 3,042,584.

Glucoamylase has been referred to in the art as glucamylase glucogenic enzyme, starch glucogenase and gama-amylase. Glucoamylase is an exo-amylolytic enzyme which catalyzes the sequential hydrolysis of glucose moieties from the non-reducing ends of starch or amylodextrin molecules. Glucoamylase is elaborated by many types of microorganisms. Certain strains of fungi belonging to the Aspergillus group such as strains belonging to the *Aspergillus niger* group and the *Aspergillus awamori* group, certain strains of the Rhizopus species and certain strains of the Endomyces species elaborate glucoamylase.

In the enzyme-enzyme conversion process, generally, a starch slurry is formed and a starch liquefying enzyme, for instance, bacterial alpha-amylase, is added thereto and the starch slurry heated to a temperature in the range of 80° to 90° C. to partially hydrolyze the starch. The partially hydrolyzed starch, which generally has a D.E. in the range of from about 10 to 20, is then treated with glucoamylase.

Alpha-amylase is an endo-amylolytic enzyme capable of promoting almost random cleavage of $\alpha$-1,4-glucosidic bonds within the starch molecule. Alpha-amylase is elaborated by many types of microorganisms such as members of the *Bacillus subtilis* species, *Aspergillus niger* and other species of the Aspergillus genus and malted cereal grains.

Alpha-amylase will not act upon the $\alpha$-1,6-glucosidic bonds in the starch molecule to any significant degree. Glucoamylase will act upon such bonds, but at a rate which is slower than is desired in commercial applications.

Recently, there has been a great deal of interest shown in the use of starch debranching enzymes for dextrose production. The use of such enzymes increases the amount of dextrose formed since they can readily act upon bonds or linkages in the starch molecules which are not acted upon by alpha-amylase or which are only slowly acted upon by glucoamylase. Debranching enzymes are generally referred to as $\alpha$-1,6-glucosidases. A number of enzymes having considerably different specificities have been identified in the art as being capable of hydrolyzing $\alpha$-1,6-glucosidic linkages. Of these, probably the two most important from the commercial standpoint are pullulanase and isoamylase. The major difference in regard to the specificity of these enzymes is that pullulanase will degrade the linear polysaccharide pullulan whereas isoamylase will not to any significant degree.

There are a number of patents which disclose methods of producing isoamylase and pullulanase and the utilization thereof. Canadian Patent 852,196 to Ueda et al. describes a process for producing isoamylase by cultivating a strain of *Escherichia intermedia* in a fermentation medium comprising dextrins, peptone and inorganic salts. U.S. Pat. No. 3,490,955 to Wallenfels et al. discloses a process for producing cellbound pullulanase from *Aerobacter aerogenes* in a culture medium wherein the carbon sources comprise maltose and pullulan or glycerin. U.S. Pat. No. 3,560,345 to Yokobayashi et al. describes a process for producing isoamylase by propagating *Pseudomonas amyloderamosa* in a culture medium containing as carbon sources, starch, starch derivatives or maltose.

Recently, there has been a great deal of interest shown in immobilized enzymes. Immobilized enzymes have a number of distinct advantages over soluble enzymes such as, for example, their use in continuous conversion systems.

Exemplary of publications which review the art directed to enzyme immobilization are the following:

Goldstein, in *Fermentation Advances*, Academic Press, New York, N.Y. (1969), pp. 391–424.

Goldstein et al., *Z. Anal. Chem.*, 243, pp. 375–396 (1968).

Kay, *Process Biochem.*, 3 (8), pp. 36–39 (1968).

Tosa et al., *Kagaku To Seibutsu*, 7 (3), pp. 147–155 (1967).

Silman et al., *Ann. Rev. Biochem.*, 35 (2), pp. 873–908 (1966).

Gryszkiewicz, *Folia Biologica*, 19 (1), pp. 119–150 (1971).

Zaborsky, "Immobilized Enzymes", CRC Press, Cleveland, Ohio (1973).

In the art of enzyme immobilization, considerable interest has been directed to the immobilization of glucoamylase. This is probably due to the fact that in many commercial enzyme processes glucoamylase is used in large amounts. The art is repleat with patents and publications directed to immobilization of glucoamylase. Exemplary of such are the following:

U.S. Pat. Nos. 2,717,852 to Stone; 3,619,371 to Crook et al.; 3,627,638 to Barker et al.; 3,672,955 to Stanley;

3,715,277 to Dinelli et al.; Japanese Patents 1360/60 and 23560/68; British Patents 1,183,259 and 1,183,260; German Patents 2,062,246, 2,146,390 and 2,206,360.

Also: Usami et al., *Hakko Kyokaishi*, 25, pp. 513–516 (1967); Barker et al., *Carbohyd. Res.*, 9, pp. 257–263 (1969);

Wilson et al., *Biotechnol. Bioeng.*, 11, pp. 349–362 (1969);

Usami et al., *J. Ferment. Tech.*, 48, pp. 506–512 (1970);

Gruesbeck, Ph.D. Thesis, Univ. Texas (1970); Bachler et al., *Biotechnol. Bioeng.*, 12, pp. 85–92 (1970); Maeda et al., *Nippon Nogei Kagaku Kaishi*, 44 (12), pp. 547–555 (1970); Maeda et al., *Hakko Kyokaishi*, 28 (10), pp. 391–397 (1970); Smiley, *Biotechnol. Bioeng.*, 13, pp. 309–317 (1971); Sorenson, MS Thesis, Purdue Univ. (1971); Miyamoto et al., *Hakko Kogaku Zasshi*, 49 (6), pp. 565–573 (1971);

Usami et al., *Hakko Kyokaishi*, 29 (4), pp. 195–199 (1971);

O'Neill et al., *Biotechnol. Bioeng.* 13, pp. 337–352 (1971); Emery et al., *Chem. Eng.* (London), No. 258, pp. 71–76 (1972); Gruesbeck et al., *Ind. Eng. Chem. Prod.*

Res. Develop, 11 (1), pp. 74–83 (1972); Beck, Ph.D. Thesis, Univ. Texas (1972); Gestrelius et al., *Biochem.*

Biophys. Acta, 276 (2), pp. 339–343 (1972); Maeda et al.,

Agr. Biol. Chem., 36 (9), pp. 1581–1594 and pp. 1839–1842 (1972); Weetal et al., *Biotechnol. Bioeng. Symp.*, No. 3, pp. 241–266 (1972); Christison, *Chem. J Ind.* (London), 5, pp. 215–216 (1972); Hough et al., *Nature*, 235, p. 389 (1972); Corno et al., *Die Staerke*, 24, pp. 420–424 (1972); Martensson et al., *Biotechnol, Bioeng.*, 14 (5), pp. 715–724 (1972); Park et al., *J. Food Sci.*, 38, pp. 358–359 (1973).

There are also a number of patents and publications which disclose the immobilization of alpha-amylase. Exemplary of such are the following:

U.S. Pat. Nos. 3,627,638 to Barker et al. and 3,715,278 to Miller; German Patents 1,282,579, 1,943,490, 2,062,246 and 2,206,360.

Also: Grubhofer et al., *Naturwissenschaften*, 40, 508, (1953); Manecke, *Pure Appl. Chem.*, 4, pp. 507–520 (1962);

Manecke et al., *Makromol. Chem.*, 51, pp. 199–216 (1962);

Bernfeld et al., *Science*, 142, pp. 678–679 (1963);

Manecke et al., *Makromol. Chem.* 91, pp. 136–154 (1966);

Fukushi et al., *J. Biochem.*, 64, pp. 283–292 (1968);

Barker et al., *Carbohyd. Res.*, 8, pp. 491–497 (1968);

Ledingham et al., *Fed. Europ. Biochem. Soc. Lett.*, 5, pp. 118–120 (1969);

Barker et al., *Carbohyd. Res.*, 14, pp. 323–326 (1970);

Barker et al., *Process Biochem.*, 5 (8), pp. 14–15 (1970);

Barker et al., *Carbohyd. Res.*, 14, pp. 287–296 (1970);

Hough et al., *Nature*, 235, p. 389 (1972);

Epton et al., *Carbohyd. Res.*, 22, pp. 301–306 (1972).

Additionally, there have been several patents and publications directed to processes for the immobilization of $\alpha$-1,6-glucosidases. Exemplary of such are the following:

British Patent 1,258,095; Martensson et al., *Biotechnol. Bioeng.*, 14 (5), pp. 715–724 (1972).

From the above noted patents and publications, it is apparent that a number of enzyme immobilization techniques have been described. These techniques include covalently bonding an enzyme to a suitable insoluble carrier, encapsulation of an enzyme within a material which is impermeable to the enzyme but permeable to the substrate and the products of the catalyzed reaction, adsorption of an enzyme on an insoluble carrier and entrapment of an enzyme within a porous polymeric material wherein the pores are of such a size that will provide free access of the substrate and the catalyzed reaction products but which are sufficiently small to prevent the escape of the enzyme.

At low starch substrate concentrations, e.g., about 1 percent, glucoamylase preparations will substantially quantitatively convert unhydrolyzed starch to dextrose. Marshall et al., *Fed. Europ. Biochem. Soc. Lett.*, 9 (2), pp. 85–88 (1970) and Fukui et al., *Agr. Biol. Chem.*, 33 (6), pp. 884–891 (1969) reported that glucoamylase preparations inherently contain alpha-amylase. When the alpha-amylase was removed from these preparations and the alpha-amylase-free glucoamylase was used to saccharify a 1 percent starch solution, lesser amounts of dextrose were formed than when glucoamylase preparations were used which inherently contained alpha-amylase.

When a glucoamylase preparation is immobilized, the resulting immobilized preparation is not capable of converting partially hydrolyzed starch to the same degree as the glucoamylase preparation from which the immobilized enzyme was prepared. Moreover, reactions catalyzed by the immobilized glucoamylase preparation are not as rapid for a given number of glucoamylase units used, especially during the latter stages of the reaction period, as are reactions catalyzed by the glucoamylase preparation used for immobilization.

Therefore, it is the principal object of the present invention to provide a method whereby substantially complete conversion of partially hydrolyzed starch to dextrose is achieved using an immobilized enzyme system.

This object and other objects of the present invention which will be apparent from the following description are attained in accordance with the present invention by contacting a partially hydrolyzed starch solution containing at least 10 percent hydrolyzed starch with an enzyme system comprising immobilized glucoamylase and alpha-amylase selected from the group consisting of soluble alpha-amylase, immobilized apha-amylase and mixtures thereof under conditions whereby substantially complete conversion of the hydrolyzed starch to dextrose is achieved.

As mentioned above, when a glucoamylase preparation is subjected to immobilization, the resulting immobilized glucoamylase does not convert partially hydrolyzed starch so rapidly nor so completely as the soluble glucoamylase preparation from which the immobilized glucoamylase is prepared. We have found that during the immobilization of a glucoamylase preparation, the alpha-amylase, which is inherently present therein, is rendered substantially inactive or inert regardless of the method of immobilization employed. This is surprising in view of the many different methods that have been disclosed for the immobilization of alpha-amylases. Although we do not wish to be bound to any theory, it is believed that the methods which have been found suitable for the immobilization of glucoamylase are not suitable for the immobilization of the alpha-amylase inherently contained in glucoamylase preparations. Apparently, the small amount of alpha-amylase which is inherently present in soluble glucoamylase preparations has a beneficial effect on the overall conversion of starch to dextrose with glucoamylase. Thus, to obtain maximum utilization of immobilized glucoamylase in the conversion of partially hydrolyzed starch to dextrose, there must also be present during the conversion soluble and/or immobilized alpha-amylase. Surprisingly, this finding is true even when the partially hydrolyzed starch has been prepared by treatment of unmodified starch with alpha-amylase and therefore would be assumed to be rendered readily susceptible to conversion with glucoamylase by such treatment. Moreover, it has been discovered that alpha-amylase added to immobilized glucoamylase is effective for increasing the conversion of partially hydrolyzed starch to dextrose even during the latter stages of the conversion. Apparently, branched dextrins are formed during the initial stages of the hydrolysis reaction which are not readily hydrolyzed by the immobilized glucoamylase but which are readily hydrolyzed by alpha-amylase and thus, the overall conversion of the starch hydrolysate is enhanced.

In the present process, the partially hydrolyzed starch may be prepared either by an enzyme or acid treatment. In the case of enzyme treatment, the partially hydrolyzed starch should have a D.E. in the range of from about 10 to about 60. At substantially higher D.E. values, the amount of dextrose formed will be limited due, presumably, to the presence of saccharides which are not readily acted upon by the immobilized glucoamylase, while at lower D.E.s, the hydrolyzed starch has a tendency to retrograde which includes the formation of a precipitate which may coat the immobilized enzymes to such an extent that their efficiency will be deleteriously affected. When a partial acid hydrolysate is used in the present process, the D.E. thereof should be in the range of from about 10 to about 30. At higher D.E.s substantial amounts of reversion products are present which are not acted upon by the present enzyme system.

The pH of the partial hydrolysate being treated may be in the range of from about 3.5 to about 6.5 and preferably will be in the range of from about 4 to about 6.

The temperature of the partial hydrolyzate being treated in the present process may vary relatively widely, but the temperature should not be sufficiently high to inactivate the enzymes within a relatively short period. Temperatures in the range of from about 30° to about 65° C. are preferred and the most preferred temperatures are in the range of from about 50° to about 60° C. At these temperatures, the possibility of undesirable microbial growth in the hydrolyzed starch is reduced and optimum catalytic activity of the enzymes is generally obtained under normal operating conditions.

The present process may be performed by a number of techniques. For instance, soluble or immobilized alpha-amylase and immobilized glucoamylase may be used concurrently or sequentially. It is preferred that they be used concurrently as, for example, when partially hydrolyzed starch is contacted with a mixture of immobilized glucoamylase and immobilized alpha-amylase. Of course, it will be realized that the alpha-amylase and glucoamylase may be immobilized on or within the same carrier and results will be obtained which are substantially equivalent to those given by mixtures of alpha-amylase and glucoamylase immobilized on separate carriers. In the case where the enzymes are used sequentially, the conversion process will comprise at least three steps in the following sequence: (1) contacting the partial hydrolysate with immobilized glucoamylase, (2) contacting the resulting hydrolysate with a soluble or immobilized alpha-amylase, and (3) contacting the resulting hydrolysate with immobilized glucoamylase. The last two steps of the sequence may be repeated a number of times depending on the conditions under which the reactions are conducted. The concurrent use of the enzymes results in greater amounts of the partially hydrolyzed starch being converted to dextrose than does sequential use except when the steps employed in sequential use are repeated a large number of times.

The preferred method of preparing the immobilized alpha-amylase for use in the present process is by covalently bonding the alpha-amylase to carriers such as cellulose, porous ceramic, macroporous synthetic resins, crosslinked dextran and similar materials.

The glucoamylase may be immobilized by any of the techniques known in the art, although, in the present process, it is preferred to use glucoamylase which has been immobilized on a cellulose derivative, such as DEAE-cellulose or immobilized covalently to an inert carrier.

A number of different types of alpha-amylase may be used, although it is preferred that saccharifying or pancreatic type alpha-amylase be used. Microorganisms such as *Bacillus subtilis* var. *amylosacchariticus* Fukumoto elaborate saccharifying type alpha-amylase. Generally, it is also preferred that alpha-amylase preparations which are to be used for immobilization have an S/L value (hereinafter defined) of at least about 3, preferably at least about 50 and most preferably a value of at least about 100.

The ratio of the activities of the enzymes used in the present process should typically be above a certain minimum value to provide optimum catalytic action. In this regard, the amounts of immobilized glucoamylase and of alpha-amylase which may be used should be sufficient to provide a ratio of dextrinizing activity (hereinafter defined) to glucoamylase activity (hereinafter defined) of at least 0.2 liquefons per glucoamylase unit. Preferably, the amounts of enzymes present will be sufficient to provide at least 1 liquefon per glucoamylase unit, and most preferably, the amounts will be sufficient to provide at least 3 liquefons per glucoamylase unit.

When the present enzyme system is used in a column or bed, or in other means whereby such can be used in a continuous manner, it is important to remove any insoluble material which may be present in the partial starch hydrolysate so that such material does not plug the column or coat the immobilized enzymes to a degree which substantially reduces the efficiency of the enzyme system. Removal of insoluble material may be accomplished in any convenient manner such as filtration, centrifugation or the like.

Immobilized $\alpha$-1,6-glucosidases may also be used in the present process. Exemplary of the preferred enzyme of this class is pullulanase. It is preferred to immobilize the pullulanase by covalently binding it to an inert carrier.

In order to more clearly describe the nature of the present invention, specific examples will hereinafter be described. It should be understood, however, that this is done solely by way of example and is intended to neither delineate the scope of the invention nor limit the ambit of the appended claims.

Expressions and procedures referred to in the present specification and claims are defined below:

DEXTROSE EQUIVALENT

Dextrose equivalent (D.E.) was determined by Method E-26 described in "Standard Analytical Methods of the Member Companies of the Corn Industries Research Foundation", Corn Refiners Association, Inc., 1001 Connecticut Avenue, N.W., Washington, D.C. 20036.

DEXTROSE CONTENT

Dextrose content was calculated from the Mathews' Index. For a discussion of Mathews' index see Cayle and Viebrock, *Cereal Chem.*, 43, 237 (1966).

The Mathews' Index was determined from measurements of optical rotation and reducing sugar content of the converted solutions. The converted solutions were diluted to about 3 percent dry solids and optical rotation (R) determined in degrees circular in a 0.2-dm., jacketed cell maintained at 25° C. using an automatic polarimeter (Bendix Scientific Instruments, Model NPL) equipped with a green light source (546.1 nm). A portion of the solution used for polarimetry was diluted four fold and titrated into 25 ml of Fehling's solution according to the method for determining D.E. enumerated above. The titre (T) so obtained is the number of mls of diluted solution which contains reducing sugars equivalent to 0.12 g of dextrose. The Mathews' Index (M) was calculated from the rotation (R) and titre (T) as follows:

$$M = RT/4$$

Percent dextrose (ash free, dry substance basis) was then calculated from the Mathews' Index by the following equation:

$$\text{Percent Dextrose} = (170 - 20\ M)/(0.2167\ M + 1.0784)$$

PREPARATION OF PARTIALLY HYDROLYZED STARCH SOLUTION

The partially hydrolyzed starch solutions used in the various analytical determinations and in the following examples were prepared using the following general procedure:

An 18° Be slurry of corn starch in water was adjusted to pH 7.0 with lime and alpha-amylase (*B. subtilis* origin, 33 liquefons per g dry starch) added. The mixture was instantaneously heated to 88° C. to gelatinize the starch and initiate enzyme action by blending with steam in a mixing jet and was then held at 88° C. for about 1 hour. The mixture was then heated to 149° C. by blending with steam under pressure in a mixing jet, held at 149° C. for about 1 minute and then cooled to 88° C. in a vacuum chamber. Additional alpha-amylase (11 liquefons per g of dry starch) was added to the mixture at 88° C. and hydrolysis continued until the desired D.E. was obtained. After cooling to 60° C., the solution was adjusted to pH 3.5 to 4 using 4 M hydrochloric acid and was then heated for 90 minutes at 100° C. to inactivate any residual alpha-amylase activity. Three percent filter aid was added and the hot hydrolyzate was filtered to remove insoluble protein and fat. The above procedure provided partially hydrolyzed starch solution having a D.E. of 12 to 20 and 31 to 34 percent dry solids.

GLUCOAMYLASE ACTIVITY

A glucoamylase activity unit (GU) is defined as the amount of enzyme which catalyzes the production of one g of dextrose per hour at 60° C. at pH 4.5 in the procedures described below.

Drum-dried partially hydrolyzed starch was used for the preparation of substrate solutions for glucoamylase activity determinations. A partially hydrolyzed starch solution having a D.E. of 12, was treated with activated carbon (Nuchar CEE, West Virginia Pulp and Paper Co.) for 45 minutes at 60° C. The carbon was removed by filtration and the filtrate was treated again with carbon and filtered in the same manner. The filtrate was concentrated to about 50 percent dry solids and was then dried on a steam-heated drum drier and ground. The drum-dried partially hydrolyzed starch contained 1.7 percent moisture and 0.5 percent ash. Substrate solutions for glucoamylase activity determinations were prepared to contain 10 g of the dried hydrolyzed starch and 2 ml of pH 4.5, 1 M sodium acetate buffer per 100 ml of solution.

ACTIVITY OF SOLUBLE GLUCOAMYLASE

Ten ml of substrate solution was pipetted into a capped reactor maintained at 60° C. One ml of glucoamylase solution containing 0.03 to 0.15 GU was added and mixed therein and the mixture maintained for one hour at 60° C. At the end of the 1-hour incubation period, enzyme action was stopped by adding a predetermined volume of 1 M sodium hydroxide solution so as to obtain a pH of 8.5 to 10.5. The mixture was then cooled to room temperature.

2.5 ml of the assay hydrolysate so obtained was pipetted into 25 ml of Fehling's solution prepared as described in the above cited method for D.E. determination. The mixture was brought to a boil and titrated with standard dextrose solution containing 5 g of dextrose per liter according to the procedure cited above for D.E. determination. A control mixture was prepared and titrated in the exact same manner as for the assay hydrolysate above except that the 1 ml of glucoamylase solution was added to the substrate solution after the 1-hour incubation period and after the addition of sodium hydroxide solution. Glucoamylase activity was calculated as follows:

$$GU/ml = 0.002\ V\ (C-A)$$

where V is the total volume (ml) of assay hydrolysate (usually 11.2 ml), C is the ml of standard dextrose solution used in the titration of the control mixture, and V is the ml of standard dextrose solution used in titration of the assay hydrolysate.

ACTIVITY OF IMMOBILIZED GLUCOAMYLASE

The activity of immobilized glucoamylase was determined by a modification of the above procedure for determining the activity of soluble glucoamylase. 10 ml of substrate solution prepared as described above was heated in a closed reactor to 60° C. A weighed amount (W) of immobilized glucoamylase containing from 3 to 10 GU was suspended in demineralized water and was diluted to 100 ml. The immobilized glucoamylase suspension was stirred and while stirring, a 1-ml aliquot of the suspension was transferred to the 10 ml of the substrate solution held at 60° C. The mixture was stirred continually for exactly 1 hour at 60° C. and was then filtered to remove the immobilized glucoamylase. 2.5 ml of the assay filtrate so obtained was added to 25 ml of Fehling's solution and titrated with standard dextrose in the manner described above for determining the activity of soluble glucoamylase. A control filtrate was prepared and titrated by the exact same steps except that one ml of water was substituted for the one ml of immobilized glucoamylase suspension. Immobilized glucoamylase activity was calculated as follows:

$$GU/g = 2.2 (C_i - A_i)/W$$

where $C_i$ is the ml of standard dextrose solution used in the titration of the control filtrate, $A_i$ is the ml of standard dextrose solution used in the titration of the assay filtrate and W is the weight (g) of immobilized glucoamylase in the 100 ml of suspension.

ACTIVITY OF ALPHA-AMYLASE

Alpha-amylase preparations were assayed by two different methods. In one method, the ability of the alpha-amylase preparation to hydrolyze soluble Lintner starch to dextrins too small to give a blue color with iodine was determined as a measure of dextrinizing activity. In the other method, the ability of the alpha-amylase preparation to produce reducing sugars by the hydrolysis of a reduced partially hydrolyzed starch was determined as a measure of saccharifying activity.

DEXTRINIZING ACTIVITY OF SOLUBLE ALPHA-AMYLASE

The dextrinizing activity of soluble alpha-amylase preparations was determined by a modification of Standard Test Method, AATCC 103, 1965, "Bacterial Alpha-Amylase Enzymes Used in Desizing, Assay of" published in the 1967 Edition of Technical Manual of the American Association of Textile Chemists and Colorists, Volume 43, pp. B-174 and B-175. The method was modified by substituting 10 ml of 1 M sodium acetate buffer, pH 5.0, for the 10 ml of pH 6.6 phosphate buffer solution used in the makeup of the buffered starch substrate. Also, 0.73 g of $CaCl_2 \cdot 2H_2O$ was added per 500 ml of buffered starch substrate. Results were calculated in terms of liquefons where one liquefon equals 0.35 Bacterial Amylase Unit.

DEXTRINIZING ACTIVITY OF IMMOBILIZED ALPHA-AMYLASE

The dextrinizing activity of immobilized alpha-amylase preparations was determined in the same manner as for soluble alpha-amylase preparations except that immobilized alpha-amylase was "diluted" for assay by suspension in 0.005 M calcium acetate solution at 30° C. A 5-ml aliquot of the suspension was added to the 10 ml of buffered starch substrate and the hydrolyzing mixture so formed was stirred continuously during the 30° C. hydrolysis step. At appropriate time intervals, 2-ml aliquots of the hydrolyzing mixture were taken and rapidly filtered and one ml of the filtrate added to the 5 ml of dilute iodine solution. Time was counted starting at the instant the 5-ml aliquot of suspension was added to the 10 ml of buffered starch substrate and finishing at the time that the 2-ml aliquot of hydrolyzing mixture was filtered.

SACCHARIFYING ACTIVITY OF SOLUBLE ALPHA-AMYLASE

Saccharifying activity of soluble alpha-amylase preparations was determined using a reduced partially hydrolyzed starch solution (RLS) as a substrate. One unit of saccharifying activity (S) was defined as the amount of enzyme which would produce an increase of 0.02 absorbance unit per minute in the procedure described below.

The RLS was prepared from a 1.8-liter sample of 12 D.E. partially hydrolyzed starch solution containing 31 percent dry solids. The partially hydrolyzed starch solution was prepared as described previously except that the final steps in its preparation comprising adjustment of the pH to 3.5 to 4.0 and heating to 90° C. to inactivate residual alpha-amylase and filtration were omitted. The hydrolyzed starch solution was adjusted to pH 6.5 to 7.0 and was heated to 70° C. Liquefying alpha-amylase preparation of B. subtilis origin containing 57,000 liquefons was added and the mixture held 3.5 hours at 70° C. The pH was adjusted to 3.5 to 4.0 and the mixture heated one hour at 100° C. 3 percent filter aid was added and the mixture was filtered. The filtrate was adjusted to pH 5.5 with 8 M NaOH solution, 10 g of DEAE-cellulose (Whatman DE 23, Reeve Angel) added, and the mixture stirred for 30 minutes at ambient temperature. The mixture was then maintained for 18 hours at 5° C. without stirring, heated to 60° C. and filtered. The filtrate was refined twice by stirring for 60 minutes at 60° C. with 16 g of activated carbon (Nuchar CEE) and about 50 g of filter aid followed by filtering. 975 ml of the twice-refined filtrate was obtained containing 34.5 percent dry solids and having a D.E. of 30.2. 400 ml of the twice-refined filtrate was cooled to about 20° C. and 0.5-g portions of sodium borohydride dissolved therein at 30-minute intervals until 6.0 g had been added. The resulting solution was stirred at ambient temperature for about 16 hours, was recooled to about 2° C. and 0.5 g of sodium borohydride dissolved therein. After stirring for 4 hours, a final 0.5-g portion of sodium borohydride was added and the solution stirred for 26 hours at ambient temperature. 435 ml of the resulting solution was refined by charging the same to an ion-exchange column containing an 89 × 2.5-cm bed of Borosorb (Calbiochem, CN 203667) and washing the charge through the column with water. The effluent (charge plus washings) was concentrated to 800 ml and then was charged to three columns placed in series as follows: an 89 × 2.5-cm bed of Borosorb, a 26 × 2.5-cm bed of strong acid resin in hydrogen form (Duolite C-3, Diamond Shamrock Chemical Co.), and a 62 × 2.5-cm bed of weak base resin in free amine form (Duolite A-6). The charge was washed through the columns with water and the effluent collected until 4.9 liters had been recovered. The effluent was concentrated to 450 ml, 0.09 g of sodium azide added and the mixture filtered through a membrane filter (Nalge Corp.) having a maximum pore size of 0.2 microns. The RLS solution so prepared had the following properties: D.E. less than 0.4, pH 6.4, 26.3 percent dry solids, 0.03 percent sulfated ash, 1.7 ppm boron.

An RLS substrate solution for measuring saccharifying activity was prepared to contain 2 g dry basis RLS, 2 ml of 1 M, pH 5.0 sodium acetate buffer, and 0.147 g of $CaCl_2 \cdot 2H_2O$ in a total volume of 100 ml. For the saccharifying activity determination, 5 ml of RLS substrate solution equilibrated to 30° C. was mixed with 5 ml of a solution of the alpha-amylase preparation diluted to contain 0.2 to 1.0 S/ml equilibrated to 30° C. The hydrolyzing mixture was incubated at 30° C. and 1-ml aliquots removed at 1, 3 and 5 minutes after combination of the enzyme and substrate solutions. Each aliquot was immediately combined with 1 ml of dinitrosalicylic acid reagent prepared according to P. Bernfeld in "Methods in Enzymology", S. P. Colowick and N. O. Kaplan, editors, Vol. I, p. 149, Academic Press, New York (1955). The mixture was heated for 5 minutes in a boiling water bath and was then cooled for at least 10 minutes in cold, running tap water (about 15° C.). The mixture was diluted by adding 10 ml of demineralized water and the absorbance of the resulting solution determined at 540 nm in a 1-cm cell. A plot of absorbance vs. incubation time was made and the slope (Y) of the plot determined in absorbance units per minute. The activity of the diluted solution of alpha-amylase preparation was calculated as follows:

Activity (S/ml) = 10 Y

S/L VALUE

The soluble alpha-amylase preparations derived from different sources and used for the preparation of immobilized alpha-amylase were classified by their S/L Value which was defined as one thousand times the saccharifying activity measured in saccharifying units (S) per g of alpha-amylase preparation divided by the dextrinizing activity measured in liquefons per g of preparation.

ACTIVITY OF SOLUBLE PULLULANASE PREPARATIONS

Pullulanase activity was determined by its hydrolytic effect on pullulan using an alkaline ferricyanide reagent to determine the maltotriose liberated. Activity was expressed in international units (IU) where one IU is the amount of pullulanase which catalyzes the liberation of 1 micromole of maltotriose per minute from a 0.5 percent solution of pullulan at pH 5.0 and 45° C.

The ferricyanide reagent was prepared by dissolving 0.85 g of potassium ferricyanide and 10 g of sodium carbonate in demineralized water and diluting to one liter. The reagent was calibrated against solutions of maltotriose (Pierce Chemical Co.). 2-ml aliquots of ferricyanide reagent were mixed in test tubes with 1-ml aliquots of maltotriose solutions containing 25, 100, 150, 200 or 250 micrograms of maltotriose per ml. The tubes were immersed in a boiling water bath for 10 minutes and then cooled for 10 minutes at ambient temperature and absorbance measured in a 1-cm cell at 420 nm. Maltotriose concentration was plotted versus absorbance and a calibration factor (C) determined from the slope of the plot.

To determine pullulanase activity, a test tube containing 9.5 ml of substrate solution comprising 8.5 ml of 0.02 M, pH 5.0 sodium acetate buffer and 1.0 ml of a solution containing 50 mg of pullulan was incubated in a 45° C. water bath for 5 minutes. A 0.5-aliquot of pullulanase solution was added to the test tube and mixed therein. At 5, 10, 15, and 20 minutes after the addition of the pullulanase solution, 1.0-ml aliquots of the reacting mixture were pipetted into test tubes containing 2 ml of the above calibrated ferricyanide reagent. The mixtures were heated, cooled, and their absorbances determined as for the calibration of the ferricyanide reagent above. Absorbance versus time was plotted and the slope (K) of the rate plot determined. Activity of the pullulanase solution was calculated from the following formula:

Activity (IU/ml) = 0.0397 CK where C is the ferricyanide reagent calibration factor (micrograms of maltotriose per ml per absorbance unit) and K is the slope of the rate plot (absorbance units per minute).

ACTIVITY OF IMMOBILIZED PULLULANASE PREPARATION

Activity of the immobilized pullulanase preparation was determined by the method described above for soluble pullulanase with the following exceptions. A suspension was formed by stirring 25 mg of immobilized pullulanase preparation in 5.0 ml of demineralized water and a 0.5-ml aliquot of the suspension added to the 9.5 ml of substrate solution to form the reaction mixture. The reaction mixture was stirred constantly during the reaction period. Aliquots were withdrawn at 5, 10, 15 and 20 minutes, were quickly filtered, and 1.0-ml portions combined with 2-ml aliquots of the ferricyanide reagent.

EXAMPLE I

This example illustrates the use of glucoamylase immobilized on DEAE-cellulose and alpha-amylase derived from different sources immobilized on aminoethyl-cellulose for converting a partially hydrolyzed starch solution to dextrose.

IMMOBILIZATION OF GLUCOAMYLASE 53.0 g of a dry glucoamylase preparation (from *Aspergillus awamori*, free of transglucosylase activity) having a glucoamylase activity of 83.2 GU $g^{-1}$ was incorporated into 3.8 liters of deionized water. The mixture was stirred for 30 minutes and filter aid added thereto. The mixture was filtered, the filter cake washed, the filtrate and washings combined, and the pH of the combined solutions adjusted to 5.5 using 4 N HCl. 13.3 g DEAE-cellulose (Whatman DE 23) was added, the mixture stirred for 60 minutes at ambient temperature and then filtered and the filter cake washed with deionized water. The recovered moist filter cake had a glucoamylase activity of 44 GU $g^{-1}$. The moist filter cake is hereinafter referred to in this example as "immobilized glucoamylase".

IMMOBILIZATION OF ALPHA-AMYLASE

Alpha-amylase derived from various sources was immobilized by coupling the alpha-amylase with activated aminoethyl-cellulose (hereinafter referred to as "activated AE").

The activated AE was prepared by slurrying 20 g of aminoethyl-cellulose (Cellex-AE manufactured by Bio-Rad Laboratories) in 500 ml of a 0.5 M phosphate buffer at pH 7, stirring for 20 minutes at ambient temperature and then maintaining the mixture for 7 hours without stirring. The mixture was filtered, the filter cake washed with deionized water and suspended for 12 hours in 500 ml of 0.5 M phosphate buffer at pH 7. 140 ml of a glutaraldehyde solution (50 percent) was added to the slurry, the slurry stirred for 90 minutes at ambient temperature, filtered and the filter cake washed with deionized water. 74.9 g of filter cake (75.2 percent moisture) was recovered.

16.0-g portions of activated AE were added to 50 ml of each of the following four alpha-amylase solutions:
a. Solution of *Bacillus subtilis* saccharifying alpha-amylase (var. *amylosacchariticus* Fukumoto, twice recrystallized, Miles Laboratories, Inc., S/L = 257) containing 0.33 mg protein per ml and having an activity of 134 liquefons per ml.
b. Solution of *Bacillus subtilis* liquefying alpha-amylase (Bacterial Type, II-A, 4x crystallized, Sigma Chemical Co., S/L = 5) containing 0.45 mg protein per ml and having an activity of 1166 liquefons per ml.

c. Solution of *Aspergillus oryzae* fungal alpha-amylase (3x crystallized, Calbiochem, S/L = 76) containing 0.45 mg protein per ml and having an activity of 322 liquefons per ml.

d. Solution of hog pancreatic alpha-amylase (2x crystallized, Worthington Biochemical Corp., S/L = 227) containing 0.70 mg protein per ml and having an activity of 290 liquefons per ml.

The mixtures were stirred for 2 hours and filtered. The filter cakes were washed with 0.005 M calcium acetate at pH 7 with small portions of 0.5 M NaCl (total 100 ml) and then with about 50 ml of 0.005 M calcium acetate solution. The immobilized alpha-amylases exhibited the following potencies:

| Alpha-Amylase | Potency (liquefons g$^{-1}$) |
|---|---|
| Immobilized saccharifying | 12.6 |
| Immobilized liquefying | 125.0 |
| Immobilized fungal | 7.3 |
| Immobilized pancreatic | 41.5 |

To each of five stirred reactors maintained in a water bath at 50° C. was added 138 g of partially hydrolyzed starch solution (pH 5.0, 16.9 D.E., 32.5 percent dry substance) prepared by the procedure described above which had been filtered through a cellulose ester membrane (HAWP 04700, 0.45 μ, Millipore Corp.) and then saturated with toluene. The purpose of the addition of the toluene was to prevent bacterial growth.

0.51 g of immobilized glucoamylase was added to each of the reactors and sufficient immobilized alpha-amylase was added to four of the reactors to provide a total of 90 liquefons of alpha-amylase activity per reactor. The reactors were continually stirred at various time intervals, samples were taken from the reactors and filtered and the filtrates assayed for percent dextrose. The results of this example are set forth in Table I.

ratio are more beneficial in the conversion of partially hydrolyzed starch to dextrose.

EXAMPLE II

This example illustrates the effect of the ratio of immobilized alpha-amylase activity to immobilized glucoamylase activity on the rate of production of dextrose.

60 g of activated AE prepared according to Example I was added to 975 ml of 0.005 M sodium acetate solution containing 5 × 10$^5$ liquefons of fungal alpha-amylase preparation derived from *Aspergillus oryzae* (Enzeco K768, Enzyme Development Corp.). After slurrying for two hours at ambient temperature, the slurry was filtered, and the filter cake washed successively with deionized water, one liter of partially hydrolyzed starch solution (3.2 percent d.s., 16.4 D.E., pH 5.0, 0.02 percent NaN$_3$) and 200 ml of 0.02 percent NaN$_3$ solution. The moist filter cake had an alpha-amylase activity of 33.3 liquefons g$^{-1}$.

SACCHARIFICATION USING IMMOBILIZED GLUCOAMYLASE AND IMMOBILIZED ALPHA-AMYLASE DERIVED FROM *ASPERGILLUS ORYZAE*

Into 6 stirred reactors each containing 462 g of partially hydrolyzed starch solution (32.0 percent d.s., 16.7 D.E., pH 5.1, 0.02 percent NaN$_3$) at 50° C. was added 1.13 g of immobilized glucoamylase prepared according to the method described in Example I and having a potency of 64.2 GU g$^{-1}$. Then into the reactors were added, respectively, 21.8 g, 10.9 g, 5.45 g, 2.72 g, 1.36 g and 0 g of immobilized fungal alpha-amylase prepared by the procedure described immediately above. The reactors were constantly stirred at 50° C. and the percent dextrose determined at various periods.

SACCHARIFICATION USING IMMOBILIZED GLUCOAMYLASE AND IMMOBILIZED ALPHA-AMYLASE OF THE PANCREATIC TYPE

Into 6 stirred reactors each containing 121 g of par-

TABLE I

Saccharification Using Immobilized Glucoamylase and Various Types of Immobilized Alpha-Amylase

| Immobilized Enzyme System | Average pH of System During Saccharification | Percent Dextrose | | | |
|---|---|---|---|---|---|
| | | 46 hrs | 70 hrs | 106 hrs | 142 hrs |
| Immobilized glucoamylase (control) | 5.1 | 71.5 | 76.3 | 79.6 | 80.9 |
| Immobilized glucoamylase and immobilized saccharifying alpha-amylase | 5.1 | 92.3 | 92.9 | 93.0 | 92.7 |
| Immobilized glucoamylase and immobilized liquefying alpha-amylase | 5.0 | 89.0 | 91.5 | 93.1 | 93.2 |
| Immobilized glucoamylase and immobilized fungal alpha-amylase | 5.2 | 87.2 | 89.7 | 91.5 | 91.9 |
| Immobilized glucoamylase and immobilized pancreatic alpha-amylase | 5.1 | 93.1 | 94.7 | 94.9 | 94.2 |

From the above table, it is seen that a combination of immobilized glucoamylase and immobilized alpha-amylase resulted in a more complete conversion of starch to dextrose than when immobilized glucoamylase alone was used. Also, the combination of immobilized enzymes resulted in a more rapid conversion of starch to dextrose. Moreover, in general, the immobilized alpha-amylase preparations prepared from the soluble alpha-amylase preparation having a high S/L tially hydrolyzed starch solution (33.4 percent d.s., 16.9 D.E., pH 5.1, saturated with toluene) at 50° C. was added 0.45 g of immobilized glucoamylase prepared according to Example I and having a potency of 44 GU g$^{-1}$. Then into the reactors were added, respectively, 4.82 g, 2.41 g, 1.20 g, 0.60 g, 0.30 g and 0 g of immobilized pancreatic alpha-amylase prepared by the procedure set forth in Example I. The reactors were constantly stirred at 50° C. and the percent dextrose determined at various periods.

The results of these experiments are shown below in Tables II and III:

TABLE II

Saccharification Using Immobilized Glucoamylase and Immobilized Fungal Alpha-Amylase

| Ratio of Alpha-Amylase Activity to Glucoamylase Activity (liquefons per GU)* | Percent Dextrose | | | | | |
|---|---|---|---|---|---|---|
| | 20 hr | 44 hr | 68 hr | 92 hr | 116 hr | 140 hr |
| 0 (Control) | 63.6 | 74.9 | 79.1 | 81.9 | 83.2 | 84.7 |
| 0.62 | 70.0 | 80.7 | 84.8 | 86.7 | 87.5 | 89.1 |
| 1.25 | 73.0 | 83.1 | 86.4 | 88.2 | 89.1 | 90.4 |
| 2.5 | 76.2 | 85.2 | 88.0 | 89.9 | 90.5 | 91.5 |
| 5.0 | 78.6 | 86.8 | 89.2 | 90.6 | 91.2 | 92.4 |
| 10.0 | 80.8 | 88.8 | 90.7 | 92.1 | 92.2 | 92.7 |

*Each reactor contained 0.5 GU g$^{-1}$ partially hydrolyzed starch

TABLE III

Saccharification Using Immobilized Glucoamylase and Immobilized Pancreatic Alpha-Amylase

| Ratio of Alpha-Amylase Activity to Glucoamylase Activity (liquefons per GU)* | Percent Dextrose | | | | | |
|---|---|---|---|---|---|---|
| | 20 hr | 44 hr | 68 hr | 92 hr | 116 hr | 140 hr |
| 0 (Control) | 62.1 | 72.3 | 77.1 | 80.1 | 81.6 | 82.5 |
| 0.62 | 69.2 | 82.7 | 87.7 | 90.1 | 90.8 | 91.2 |
| 1.25 | 77.2 | 88.4 | 92.0 | 93.1 | 93.7 | 93.4 |
| 2.5 | 81.8 | 91.2 | 93.4 | 94.3 | 94.3 | 94.1 |
| 5.0 | 85.1 | 92.9 | 94.6 | 95.2 | 95.2 | 94.7 |
| 10.0 | 87.6 | 94.0 | 95.2 | 95.6 | 95.1 | 95.6 |

*Each reactor container 0.5 GU g$^{-1}$ partially hydrolyzed starch

From the above tables it is seen that as the ratio of alpha-amylase activity to glucoamylase activity is increased, the faster and the more complete is the conversion. However, at the higher ratios the difference in the conversion is small which indicates that there is a maximum ratio where no substantial increase in conversion is obtained.

EXAMPLE III

This example illustrates the utilization of covalently immobilized glucoamylase and various other immobilized enzymes.

IMMOBILIZATION OF GLUCOAMYLASE 20 g of DEAE-cellulose (Whatman DE 23) was slurried in 500 ml of 1N NaOH, stirred for 30 minutes at ambient temperature and the slurry filtered. The filter cake was slurried in 30 ml of acetone containing 4.0 g cyanuric chloride for 1 minute and then 600 ml of 20 percent acetic acid solution was added. After about one minute, the slurry was filtered, the filter cake washed with deionized water and suspended in 800 ml of a 50 percent (v/v) mixture of 0.2 M tris(hydroxymethyl)aminomethane and 5N HCl. After stirring for 7 minutes, 600 ml of 20 percent acetic acid was added to the slurry and stirring continued for another minute. The slurry was filtered, the filter cake washed extensively with deionized water and then with 500 ml of acetone. The filter cake was dried by applying partial vacuum thereto. 19 g of filter cake was recovered.

The filter cake was added to 2000 ml of a glucoamylase solution (3.8 GU ml$^{-1}$) free of transglucosylase prepared by thoroughly dialyzing a glucoamylase concentrate against tap water and then against pH 8.1 borate buffer (0.05 M). After stirring for 20 hours at ambient temperature, the slurry was filtered and the filter cake washed extensively with deionized water. The moist filter cake was then suspended in 500 ml of 1M NaCl, stirred 30 minutes and filtered. The filter cake was washed with 500 ml of a 1M NaCl solution and then with deionized water. The filter cake weighed 74.3 g and had an activity of 15 GU g$^{-1}$.

IMMOBILIZATION OF PULLULANASE

Aerobacter aerogenes ATCC 15050 was propagated and the pH of the fermentation broth was adjusted to 7 by the addition of a 0.2 M solution of NaH$_2$PO$_4$. 80 g of Triton X-100 (Rohm & Haas) was also added to the broth. The broth was stirred for 16 hours at 35° C., centrifuged at 18,000 × g for 10 minutes and the sediment discarded. The supernate had a pullulanase activity of 1.07 IU ml$^{-1}$.

The pH of a 4000-ml portion of the supernate was adjusted to 7.6 by the addition of a solution of 0.2 M Na$_2$HPO$_4$ and 6 g of DEAE-Sephadex A-50 (Pharmacia) was added. The slurry was stirred for 30 minutes at ambient temperature, filtered and the filter cake washed with 1000 ml of deionized water. The filter cake was suspended in 100 ml of pH 7.0, 0.01 M phosphate buffer containing 5.4 g NaCl and stirred for 30 minutes. The slurry was filtered and the filtrate concentrated to 290 ml by ultrafiltration in an Amicon model 401 ultrafiltration cell equipped with an XM-50 membrane. This filtrate was then dialyzed against deionized water to obtain a solution having a pullulanase activity of 10.5 IU ml$^{-1}$.

80 g of Whatman standard grade powdered cellulose was suspended in 500 ml of 5 M NaOH solution and allowed to stand for 16 hours. The supernate was removed by decantation and the cellulose washed several times with deionized water. The supernate was again removed by decantation and the cellulose filtered and suspended in 500 ml of deionized water. A 200 ml aliquot of the suspension containing about 20 g dry basis cellulose was adjusted to pH 10.5 by the addition of 1 M NaOH solution. 50 ml of a solution containing 5 g of cyanogen bromide was added and during a 45-minute reaction period, the pH of the mixture was maintained in the range of from 10.0 to 10.5 by the periodic addition of 1 M NaOH solution. The cyanogen bromide-activated cellulose was collected by filtration, the filter cake washed with 1000 ml of deionized water and then with 200 ml of 0.01 M sodium phosphate buffer at pH 7.9.

200 ml of the dialyzed filtrate having a pullulanase activity of 10.5 IU ml$^{-1}$ was adjusted to pH 7.9 by the addition of 0.2 M Na$_2$HPO$_4$ solution. 10 g of the cyanogen bromide-activated cellulose was added, the suspension stirred for 16 hours at a temperature of about 3° C. and filtered, and the filter cake washed with 50 ml of 1 M NaCl solution. The washed filter cake had a pullulanase activity of 80.2 IU g$^{-1}$.

IMMOBILIZATION OF SACCHARIFYING ALPHA-AMYLASE 7 g of cyanogen bromide-activated cellulose (prepared by the procedure described above) was added to 99 ml of cold 0.1 M phosphate buffer at pH 8 having dissolved therein sufficient saccharifying alpha-amylase (*B. subtilis var. amylosacchariticus*) to obtain an activity of 260 liquefons ml$^{-1}$. The suspension was stirred for 20 hours while being maintained at 5° C. and was filtered, the filter cake washed, successively, with 0.1 M phosphate buffer, with deionized water, with 2 percent Lintner starch solution at pH 5 and finally again with deionized water.

The washed filter cake had an alpha-amylase activity of 74 liquefons g$^{-1}$.

UTILIZATION OF THE IMMOBILIZED ENZYMES

Four stirred reactors each containing 400 ml of partially hydrolyzed starch solution (25.6 percent dry substance, 12.1 D.E., pH 5.2) were set up. The immobilized enzymes prepared as described above were introduced into the reactors and stirring commenced. Periodically, the D.E.s of the converted solutions were determined. After 70 hours, the contents of each of the reactors was filtered, the filter cakes washed extensively with deionized water and then added to 400 ml of partially hydrolyzed starch solution (30.8 percent dry substance, 12.1 D.E., pH 5.2, 0.02 M in acetate buffer). Periodically, the D.E.s of the converted solutions were determined. After 94 hours the contents of each of the reactors were filtered, the filter cakes washed extensively with deionized water and then added to 400 ml of partially hydrolyzed starch solution (30.8 percent dry substance, 12.1 D.E., pH 5.2, 0.02 M in acetate buffer). The D.E.s of the converted solutions were determined periodically. The results of these experiments are set forth in Tables IV to VII below:

TABLE IV

Saccharification Using Immobilized Glucoamylase

| Immobilized Enzyme System | D. E. (Dextrose Equivalent) | | | |
|---|---|---|---|---|
| | 22 hrs. | 46 hrs. | 70 hrs. | 94 hrs. |
| 10.7 g of immobilized glucoamylase (first use) having a total activity of 160.5 GU | 70.3 | 77.8 | 79.8 | |
| Filter cake of immobilized glucoamylase (second use) recovered from converted solution above after 70 hours of use. | 74.6 | 78.8 | 80.9 | 86.5 |
| Filter cake of immobilized glucoamylase (third use) recovered from converted solution above after 94 hours of use. | 74.8 | 82.4 | 84.9 | |

TABLE V

Saccharification Using Immobilized Glucoamylase and Pullulanase

| Immobilized Enzyme System | | D.E. (Dextrose Equivalent) | | | |
|---|---|---|---|---|---|
| | | 22 hrs. | 46 hrs. | 70 hrs. | 94 hrs. |
| 10.7 g of immobilized glucoamylase having a total activity of 160.5 GU (first use). | 0.5 g of immobilized pullulanase having a total activity of 4 IU (first use). | 80.5 | 85.1 | 87.1 | |
| Filter cake of immobilized glucoamylase and pullulanase (second use) recovered from converted solution above after 70 hours of use. | | 80.0 | 84.4 | 86.2 | 87.7 |
| Filter Cake of immobilized glucoamylase and pullulanase (third use) recovered from converted solution above after 94 hours of use. | | 79.4 | 84.2 | 88.6 | |

TABLE VI

Saccharification Using Immobilized Glucoamylase, Pullulanase and Saccharifying Alpha-Amylase

| Immobilized Enzyme System | | | D.E. (Dextrose Equivalent) | | | |
|---|---|---|---|---|---|---|
| | | | 22 hrs. | 46 hrs. | 70 hrs. | 94 hrs. |
| 10.7 g of immobilized glucoamylase having a total activity of 160.5 GU. | 0.5 g of immobilized pullulanase having a total activity of 4 IU. | 2.5 g of immobilized alpha-amylase having a total activity of 18.5 liquefons | 96.9 | 96.8 | 95.8 | |
| Filter cake of immobilized glucoamylase, pullulanase and alpha-amylase (second use) recovered from converted solution above after 70 hours of use. | | | 91.2 | 95.0 | 95.4 | 95.4 |
| Filter cake of immobilized glucoamylase, pullulanase and | | | | | | |

TABLE VI-continued

Saccharification Using Immobilized Glucoamylase, Pullulanase and Saccharifying Alpha-Amylase

| Immobilized Enzyme System | D.E. (Dextrose Equivalent) | | | |
|---|---|---|---|---|
| | 22 hrs. | 46 hrs. | 70 hrs. | 94 hrs. |
| alpha-amylase (third use) recovered from converted solution above after 94 hours of use. | | 86.0 | 92.4 | 93.2 |

TABLE VII

Saccharification Using Immobilized Glucoamylase and Saccharifying Alpha-Amylase

| Immobilized Enzyme System | | D. E. (Dextrose Equivalent) | | | |
|---|---|---|---|---|---|
| | | 22 hrs. | 46 hrs. | 70 hrs. | 94 hrs. |
| 10.7 g of immobilized glucoamylase having a total activity of 160.5 GU (first use). | 2.5 g of immobilized alpha-amylase having a total activity of 18.5 liquefons (first use). | 95.5 | 96.4 | 95.9 | |
| Filter cake of immobilized glucoamylase and alpha-amylase (second use) recovered from converted solution above after 70 hours of use. | | 88.4 | 93.1 | 94.6 | 95.1 |
| Filter cake of immobilized glucoamylase and alpha-amylase (third use) recovered from converted solution above after 94 hours of use. | | 83.0 | 89.4 | 90.7 | |

What is claimed is:

1. A process for converting starch to dextrose comprising treating starch with alpha-amylase to obtain a partially hydrolyzed starch solution containing at least 10 percent hydrolyzed starch and then treating the partially hydrolyzed starch solution with an enzyme system comprising immobilized glucoamylase selected from the group consisting of glucoamylase covalently bonded to an insoluble carrier and glucoamylase adsorbed on an insoluble carrier and immobilized alpha-amylase selected from the group consisting of alpha-amylase covalently bonded to an insoluble carrier and alpha-amylase adsorbed on an insoluble carrier under conditions whereby a hydrolysate containing at least about 92 percent dextrose on an ash free, dry basis is produced.

2. A process for converting starch to dextrose as defined in claim 1, wherein the amount of immobilized glucoamylase and the amount of immobilized alpha-amylase are such as to provide a ratio of dextrinizing activity to glucoamylase activity of at least 0.2 liquefons per glucoamylase unit.

3. A process for converting starch to dextrose as defined in claim 1, wherein the amount of immobilized glucoamylase and the amount of immobilized alpha-amylase are such as to provide a ratio of dextrinizing activity to glucoamylase activity of at least 1 liquefon per glucoamylase unit.

4. A process for converting starch to dextrose as defined in claim 1, wherein the amount of immobilized glucoamylase and the amount of immobilized alpha-amylase are such as to provide a ratio of dextrinizing activity to glucoamylase activity of at least 3 liquefons per glucoamylase unit.

5. A process for converting starch to dextrose as defined in claim 1, wherein the immobilized alpha-amylase is prepared from a soluble alpha-amylase preparation having a S/L value of at least about 3.

6. A process for converting starch to dextrose as defined in claim 1, wherein the immobilized alpha-amylase is prepared from a soluble alpha-amylase preparation having a S/L value of at least about 50.

7. A process for converting starch to dextrose as defined in claim 1, wherein the immobilized alpha-amylase is prepared from a soluble alpha-amylase preparation having a S/L value of at least about 100.

8. A process for converting starch to dextrose as defined in claim 1, wherein the partially hydrolyzed starch is contacted with a mixture of immobilized glucoamylase and immobilized alpha-amylase.

9. A process for converting starch to dextrose as defined in claim 1, wherein the alpha-amylase and the glucoamylase are immobilized on or within the same carrier.

10. A process for converting starch to dextrose as defined in claim 8, wherein the partially hydrolyzed starch solution is contacted, sequentially, with immobilized glucoamylase, with immobilized alpha-amylase and with immobilized glucoamylase.

11. A process for converting starch to dextrose as defined in claim 1, wherein the partially hydrolyzed starch solution is prepared by an enzyme treatment and has a D.E. from about 10 to about 60.

12. A process for converting starch to dextrose as defined in claim 1, wherein the temperature of the partially hydrolyzed starch solution being contacted with the enzyme system is from about 30° to about 65° C.

13. A process for converting starch to dextrose as defined in claim 12, wherein the pH of the partially hydrolyzed starch solution being contacted with the enzyme system is from about 3.5 to about 6.

14. A process for converting starch to dextrose as defined in claim 1, wherein the enzyme system includes an immobilized alpha-1,6-glucosidase.

15. A process for converting starch to dextrose as defined in claim 14, wherein the immobilized alpha-1,6-glucosidase is immobilized pullulanase.

16. A process for converting starch to dextrose as defined in claim 15, wherein the pullulanase is covalently bonded to an inert carrier.

17. A process for converting starch to dextrose as defined in claim 1, wherein the glucoamylase is adsorbed on a cellulose derivative.

* * * * *